(12) United States Patent
Otto et al.

(10) Patent No.: US 6,904,621 B2
(45) Date of Patent: Jun. 14, 2005

(54) URINE COLLECTION DEVICE

(75) Inventors: Edgar A. Otto, Boca Raton, FL (US); Gregory M. Otto, Delray Beach, FL (US)

(73) Assignee: Preferred Medical Devices, Inc., Boca Raton, FL (US)

( * ) Notice: Subject to any disclaimer, the term of this patent is extended or adjusted under 35 U.S.C. 154(b) by 0 days.

(21) Appl. No.: 10/700,192

(22) Filed: Nov. 3, 2003

(65) Prior Publication Data

US 2004/0187200 A1 Sep. 30, 2004

Related U.S. Application Data

(63) Continuation-in-part of application No. 10/401,260, filed on Mar. 27, 2003, now Pat. No. 6,857,137.

(51) Int. Cl.⁷ .............................. A47K 11/12
(52) U.S. Cl. ........................ 4/144.1; 604/347
(58) Field of Search ................. 604/347; 4/144.1–144.4

(56) References Cited

U.S. PATENT DOCUMENTS

| | | | |
|---|---|---|---|
| 2,749,558 A | | 6/1956 | Lent et al. |
| 3,485,233 A | * | 12/1969 | Cord ........................... 600/574 |
| 3,626,941 A | | 12/1971 | Webb |
| 3,776,231 A | * | 12/1973 | Holbrook et al. ........... 604/322 |
| 4,023,216 A | * | 5/1977 | Li .............................. 4/144.3 |
| 4,298,006 A | * | 11/1981 | Parks ......................... 607/106 |
| 4,360,933 A | * | 11/1982 | Kimura et al. ................. 4/301 |
| 4,683,598 A | * | 8/1987 | Jones ............................. 4/301 |
| 4,747,166 A | | 5/1988 | Kuntz |
| 5,176,667 A | * | 1/1993 | DeBring ..................... 604/356 |
| 5,269,030 A | | 12/1993 | Pahno et al. |
| 5,449,347 A | | 9/1995 | Preen et al. |
| 5,466,229 A | | 11/1995 | Elson et al. |
| 5,496,300 A | * | 3/1996 | Hirsch et al. ............... 604/427 |
| 5,551,097 A | | 9/1996 | Short |
| 5,681,297 A | | 10/1997 | Hashimoto et al. |
| 5,701,612 A | | 12/1997 | Daneshvar |
| 5,809,586 A | | 9/1998 | Kitamura |
| 5,842,237 A | | 12/1998 | Hargest et al. |
| 5,894,608 A | * | 4/1999 | Birbara ....................... 4/144.3 |
| 6,001,086 A | | 12/1999 | Rammacher |
| 6,009,570 A | | 1/2000 | Hargest et al. |
| 6,110,159 A | | 8/2000 | Tsujita et al. |
| 6,238,378 B1 | | 5/2001 | Perez |
| 6,311,339 B1 | * | 11/2001 | Kraus ......................... 4/144.3 |

* cited by examiner

Primary Examiner—Charles E. Phillips
(74) Attorney, Agent, or Firm—Akerman Senterfitt; J. Rodman Steele, Jr.; Michael K. Dixon

(57) ABSTRACT

A portable urine collection device having a closed loop system that is easily usable by a human. The urine collection device includes a urine collection receptacle for receiving a fluid from a human. The urine collection receptacle may be coupled to a reservoir with a conduit. The reservoir may be a disposable plastic bag having markings for determining the amount of urine contained in the bag. The urine collection receptacle may have multiple configurations and may be configured to receive urine from a female or male human, or both. The urine collection device may also include a pump for pumping urine from the urine collection receptacle to the reservoir without components of the pump contacting the urine being pumped.

33 Claims, 3 Drawing Sheets though the device can be used with the help of another person, if desired. The urine collection device greatly decreases the possibility of infection in those humans wearing the device.

URINE COLLECTION DEVICE

CROSS REFERENCE TO RELATED APPLICATIONS

This application is a continuation-in-part of U.S. application Ser. No. 10/401,260, filed Mar. 27, 2003 now U.S. Pat. No. 6,857,137.

FIELD OF THE INVENTION

This invention is directed generally to urine collection devices, and more particularly, to portable urine collection devices for collecting urine from incapacitated humans who are unable to use conventional facilities.

BACKGROUND

Removal of urine from incapacitated humans has been undertaken using a variety of devices and methods with mixed amounts of success. For instance, diapers have been used to remove urine from humans. While diapers collect most of the urine produced by a human, diapers leak, which can cause rashes on humans. In addition, diapers must be changed to function adequately. Otherwise, urine may leak from the diaper. For at least these reasons, diapers are not the most desirable choice of devices for collecting urine from a human.

Another device commonly used to collect urine from incapacitated humans who are unable to use conventional toilets is a bedpan. Bedpans have been used successfully but produce undesirable odors and are, at times, unsightly. In addition, bedpans often require the assistance of a nurse to use. While a nurse is respectful of a human's privacy, nurses often make humans uncomfortable.

Catheters are also commonly used to remove urine from humans. Catheters are typically composed of small diameter tubing that is placed inside the urethra of a human. While catheters are efficient at removing urine from humans, catheters often causes a high amount of infection. Thus, a need exists for removing urine from men without causing infection.

Still another class of devices that has been developed more recently are urine suction devices. Urine suction devices transport urine from a human to a collection device using pumps, gravity and other forces. For instance, U.S. Pat. No. 6,311,339 is directed to a suction collector that receives urine in a well through a flexible urine collection conduit. The suction collector includes a vacuum for transporting urine from a human to a well. The suction collector is operable once a urine collection receptacle is sealed against a human's skin surface and the pump is actuated. While the suction collector has overcome some of the disadvantages of the diaper and the bedpan, the suction collector is not without its inconveniences.

Thus, a need exists for a urine collector that is easy to use by incapacitated humans.

SUMMARY OF THE INVENTION

This invention is a urine collection device for collecting urine from humans who may be incapacitated and unable to used conventional toilets. In addition, the urine collection device may also be used by humans in standing, seated, or prone positions, such as by pilots, drivers, or others. The urine collection device may be a sterile device capable of receiving urine from a human. Use of the urine collection device results in no contamination of the components forming the device, except for a urine collection receptacle, a conduit, a reservoir, and a check valve.

The urine collection device may include a urine collection receptacle configured to operate automatically and collect urine from a human in a leak free manner. In at least one embodiment, the urine collection receptacle may include upper and lower surfaces forming an inlet. The upper surface may be positioned at an angle relative to the lower surface such that when the receptacle is placed in contact with a crotch of a human, the human may urinate without leakage or spillage. In addition, the receptacle may be sized such that the receptacle may be placed on a surface, such as a bed, and placed in contact with a crotch of a prostrate human while allowing the human to urinate without spillage or leakage. The receptacle may also include a neck adapted to collect urine and drain the urine to a conduit. The receptacle may further include a handle facilitating easier handling of the receptacle.

The urine collection receptacle may be coupled to a reservoir using a conduit. The reservoir may be portable and releasably coupled to the conduit between the urine collection receptacle and the reservoir. A check valve may be positioned along the conduit proximate to the collection receptacle or attached to the receptacle for preventing urine from flowing back into the collection receptacle. The check valve prevents backflow of urine into the urine collection receptacle in the event the conduit is inverted. Thus, the check valve prevents spillage of urine from the urine collection receptacle once the urine has been received by the conduit.

The urine collection device may also include a pump coupled to the conduit for pumping urine from the urine collection receptacle to the reservoir. The pump may be capable of pumping urine without contacting the urine while the pump may be in contact with a portion of the conduit between the urine collection receptacle and the reservoir. In one embodiment, the pump is a peristaltic pump. This configuration enables the device to be quickly setup for different humans.

The urine collection device may include a stand for supporting the reservoir, the pump, and the conduit. The stand may be portable and include a plurality of wheels for moving the stand. The stand may include a container that is releasably coupled to the stand for supporting the reservoir. The stand may also include a towelette dispenser for storing sanitary cleansing products.

The urine collection device may include support device for supporting the urine collection receptacle when the urine collection receptacle is not in use. An on/off switch may be coupled to the support device for controlling the pump. The on/off switch may be configured so that the pump is turned on when the urine collection receptacle is removed from the support device, and the pump is turned off when the urine collection receptacle is hung on the support device. This configuration renders the urine collection device automatic in the sense that a human need only remove the receptacle from the support device and place it in position between the human's legs. Once the receptacle is removed from the support device, the pump begins operating. Thus, once the receptacle is placed between a human's legs, the human may begin urinating and the pump removes urine from the receptacle and deposits it into the reservoir. The pump shuts off once the receptacle is returned to the support device. In at least one embodiment, the pump may run for a short period of time, such as about 10 seconds, after the receptacle has been placed on the support device so that any remaining urine in the urine collection receptacle or in the conduit may be transported to the reservoir.

An advantage of this invention is that the urine collection device is portable and enables humans to urinate in any location with comfort and without the assistance of a nurse.

Another advantage of this invention is that the urine collection device is operable by simply lifting a urine collection receptacle from a support device and urinating in the urine collection receptacle.

Yet another advantage of this invention is that the urine collection device is a closed system wherein every portion of the urine collection device that contacts urine may be easily removed from the device and disposed. Thus, this system is easy to clean.

Still another advantage of this invention is that the reservoir is marked to indicate the volume of urine contained in the reservoir for analytical purposes.

Another advantage of this invention is that the urine collection device includes a unisex version of the urine collection receptacle.

Yet another advantage of this invention is that the urine collection device prevents urine from flowing backwards through the conduit back into the urine collection receptacle after urine has entered the conduit.

Another advantage of this invention is that the urine collection receptacle is ergonomically configured and includes an inlet configured to contact a crotch of a female human and enable the human to urinate without spillage or leakage.

Still another advantage of this invention is that the reservoir of the urine collection device may have a capacity to receive multiple urinations before reaching its capacity, and, in at least one embodiment, may contain urine equal to about six urinations.

These and other features and advantages of the present invention will become apparent after review of the following drawings and detailed description of the disclosed embodiments.

BRIEF DESCRIPTION OF THE DRAWINGS

The accompanying drawings, which are incorporated in and form a part of the specification, illustrate embodiments of the presently disclosed invention and, together with the description, disclose the principles of the invention.

DETAILED DESCRIPTION OF THE INVENTION

Figure 1:
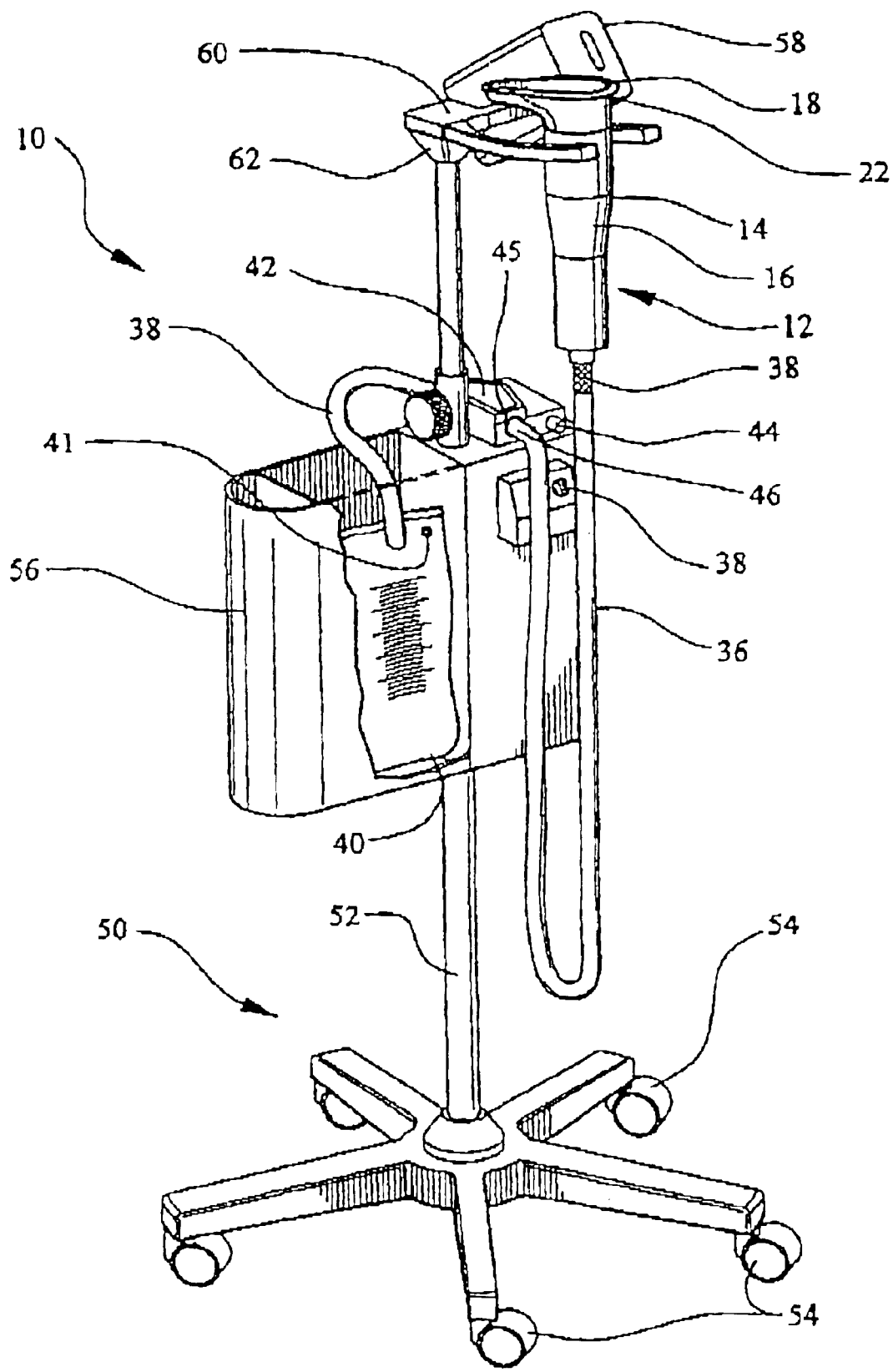
FIG. 1 is a perspective view of an exemplary embodiment of a urine collection device.

As shown in FIG. 1, this invention is a urine collection device 10 for collecting urine from humans. More specifically, urine collection device 10 may be used to collect urine from bedridden humans, humans who are incapacitated and unable to use conventional toilets, and others. Urine collection device 10 may also be used to collect urine from humans in various positions, such as, but not limited to, a seated position, a standing position, a prostrate position, and other positions.

In one embodiment, urine collection device 10 includes one or more urine collection receptacles 12 for receiving urine from a human. Urine collection receptacle 12 is configured so that a human may urinate into the urine collection receptacle 12 without assistance from a nurse or other assistant. Urine collection receptacle 12 may be configured in male and female versions or in a unisex version configured to be used by both sexes. A male version 14, as shown in FIG. 1, may be a cylinder 16 have an opening 18 configured to receive a male human penis. Opening 18 may include a flexible perimeter 22 coupled to opening 18 to improve the sealing ability of the urine collection receptacle 12. Male version 14 is not limited to the configuration shown in FIG. 1. Instead, male version 14 may have configurations other than the embodiment shown.

Figure 2:
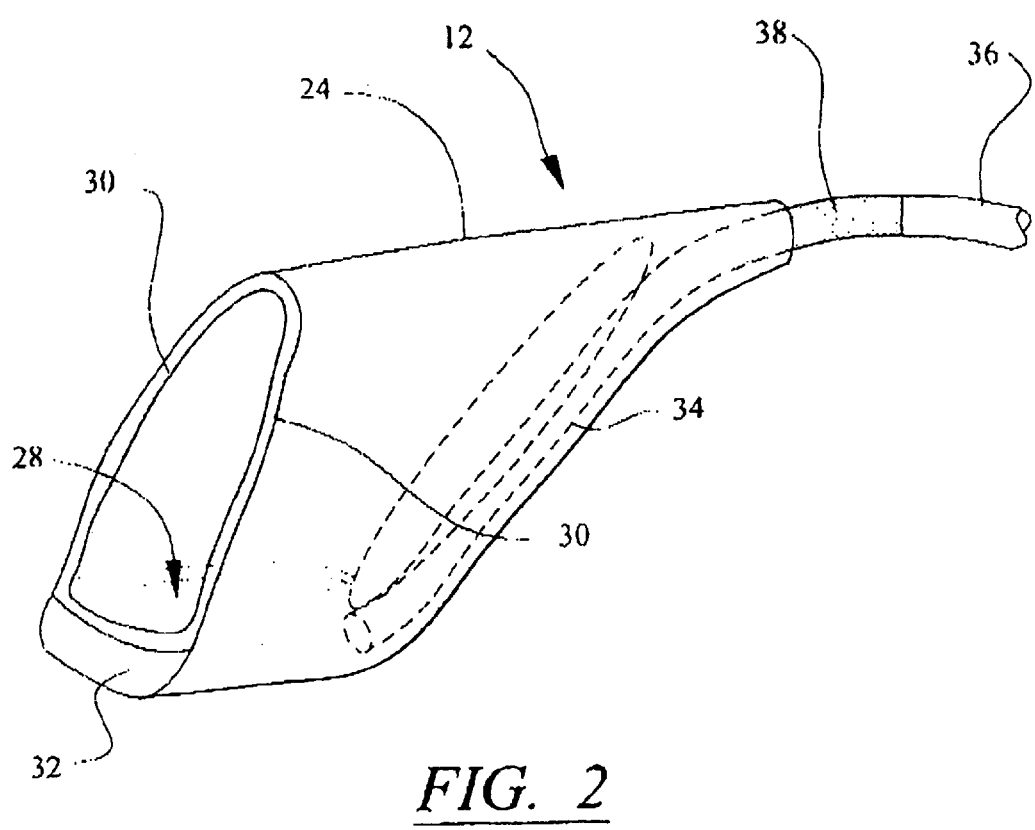
FIG. 2 is a perspective view of unisex version of a urine collection receptacle.

A unisex version 24 of the urine collection receptacle 12, as shown in FIG. 2, is configured to receive urine from a female human being without significant spillage. Unisex version 24 conforms to a skin surface of a female human being proximate to a urethra so that urine expelled from the urethra collects in urine collection receptacle 12. The unisex version 24 includes a collection basin 28 that is configured to collect urine. The collection basin 28 may be a cavity formed in the body of the uinsex version 24. Collection basin 28 is formed by sides 30 and lip 32. Sides 30 are configured to fit between legs of a female or male human. A tube 34 is positioned in the urine collection receptacle 12 to draw urine from collection basin 28.

Figure 3:
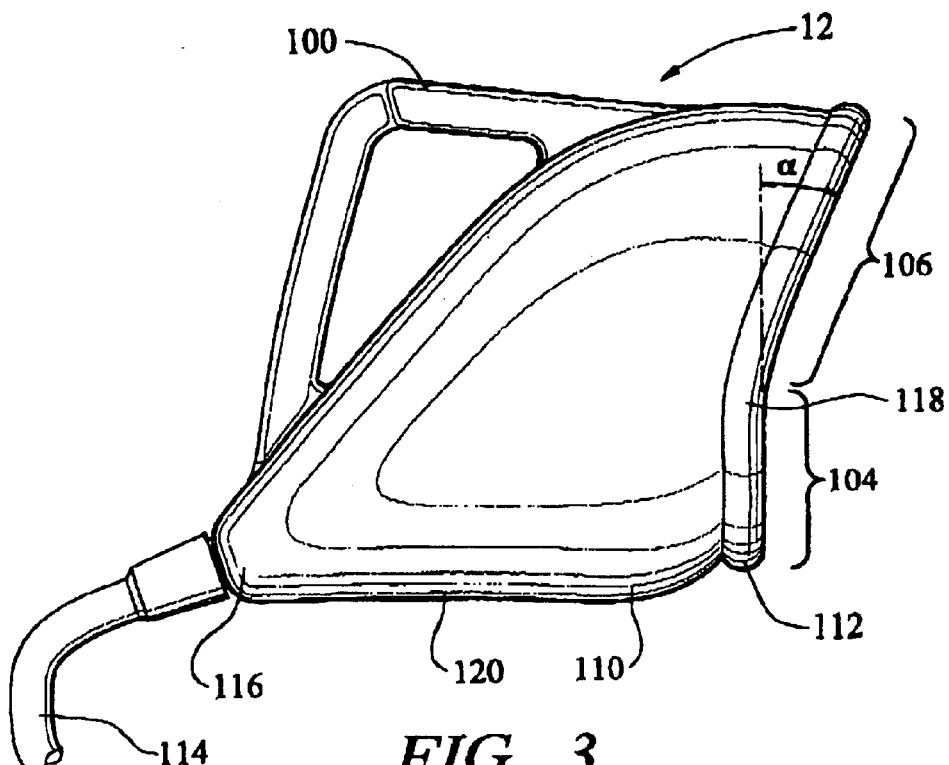
FIG. 3 is a front side view of an alternative embodiment of the urine collection receptacle.
Figure 4:
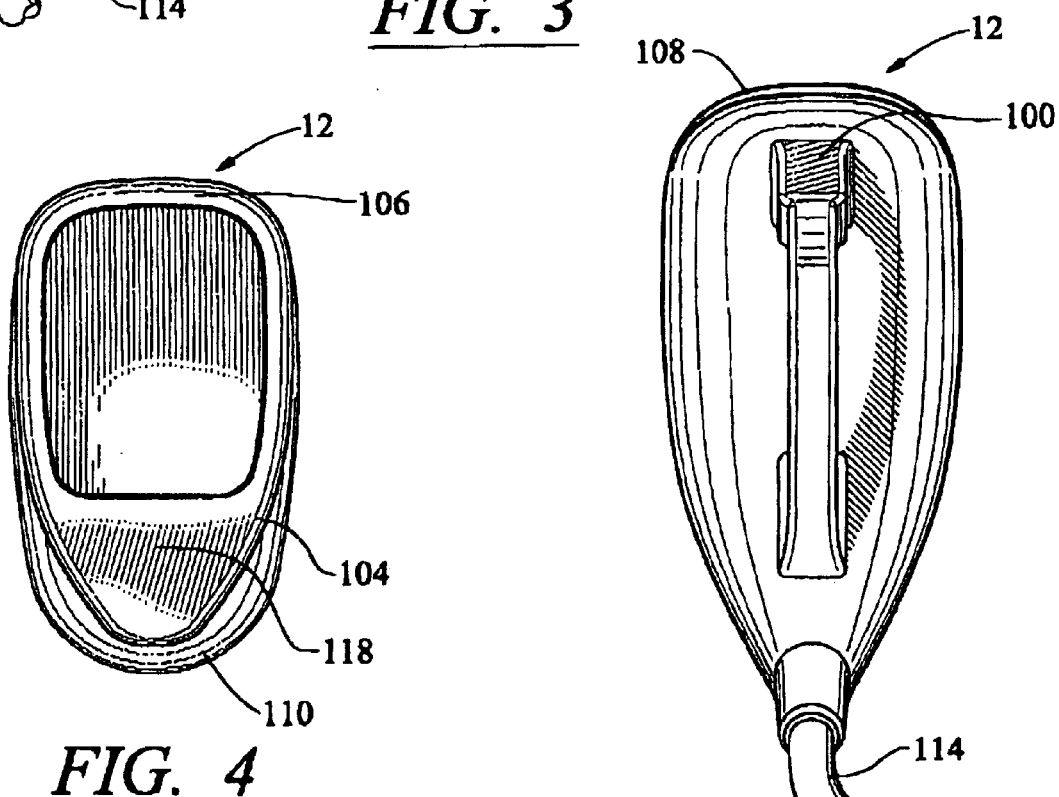
FIG. 4 is a right side view of the alternative embodiment of FIG. 3.
Figure 5:
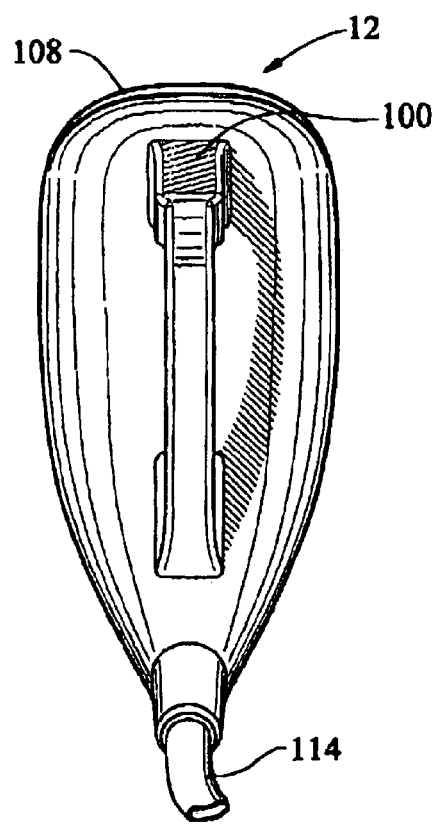
FIG. 5 is a rear view of the alternative embodiment of FIG. 3.

An alternative embodiment of the unisex version 24 of the urine collection receptacle 12, as shown in FIGS. 3–5, may include one or more handles 100 that enable a user to easily move the urine collection receptacle 12 between the user's legs. The handle 100 may be integrally formed in the receptacle 12 or may be attached to the receptacle 12 after formation of the receptacle 12. The inlet 102 of the unisex version 24 may also be ergonomically shaped to be sealed to the crotch of a female human to enable leak free use. More specifically, the inlet 102 may have a generally concave shape. As shown in FIG. 3, the inlet 102 may be formed from a lower surface 104 and an upper surface 106. The upper surface 106 may be at an angle a of between about 5 degrees and about 35 degrees. Preferably, the upper surface 106 may be at an angle a of about 25 degrees.

The inlet 102 may also include a seal 108 for sealing the urine collection receptacle 12 to the crotch of a female human in such a position to enable the user to urinate into the receptacle 12 without any of the urine spilling out of the receptacle 12. In at least one embodiment, the seal 108 may be integrally formed into the receptacle 12. The seal 108 may or may not be formed from the same material used to form the receptacle 12. In at least one embodiment, the seal 108 may be formed from a pliable material. A lip 118 may be included in the receptacle 12 for reducing the likelihood of spillage of the urine from the receptacle 12. The lip 118 prevents urine from spilling out of the urine collection receptacle 12 in the event the receptacle 12 is turned over or otherwise knocked over. The lip 118 may or may not be integrally formed with the receptacle 12.

The unisex version 24 of the urine collection receptacle 12 shown in FIGS. 3–5 may be adapted to receive urine from a human lying prostrate without risk of spilling the urine out of the receptacle 12. For instance, the receptacle 12 may include a collection neck 110 for collecting urine. The neck 110 may extend below a lower edge 112 of the seal 108. In addition, a conduit 114 may be coupled to a corner 116 of the receptacle 12 so that all of the urine contained in the receptacle 12 may be removed. A bottom surface 120 may be configured so that the receptacle 12 may rest on a relatively flat surface without falling over, while allowing the urine to collect in the neck 110 and drain into the conduit 114. The urine collection receptacle 12 may also be sized such that the receptacle 12 may rest on a flat surface, such as a bed, while the seal 108 is in contact with a crotch of a human user in a manner enabling the human user to urinate into the receptacle 12 while in a prone position; thus, the urine collection receptacle 12 remains upright while in use. This configuration enables at least substantially all of the urine disposed into the urine collection receptacle 12 to be passed to the conduit 36. Thus, the urine does not remain in the urine collection receptacle 12 after being briefly collected by the urine collection receptacle.

In at least one embodiment, the urine collection receptacle 12 may be formed from a disposable material, such as, but not limited to, a plastic or other appropriate material. The urine collection receptacle 12 may also be reusable be the same human or used by other humans after being cleansed with cleaners or other products to disinfect the urine collection receptacle 12.

In one embodiment, urine collection receptacle 12 is releasably coupled to a conduit 36 using, for instance, a quick connect fitting 38. Use of quick connect device 38 enables male version 14 and unisex version 24 of urine collection receptacle 12 to be interchanged with ease. Urine collection receptacle may also be attached to conduit 38 using devices other than quick connect fitting 38. For instance, urine collection receptacle 12 may be coupled to conduit 36 using one or more adhesives, mechanical connectors, and other coupling devices.

Urine collection receptacle 12 is coupled to a reservoir 40 using conduit 36. Conduit 36 may be made from rigid or flexible materials. In one embodiment, conduit 36 is a flexible tubing that is transparent so that the flow of urine through the tubing to reservoir 40 can be monitored. Conduit 36 may also be opaque and formed from any color. Reservoir 40 may be formed from any device capable of holding urine. In one embodiment, reservoir 40 is a transparent, flexible, plastic bag that is marked to indicate the amount of fluid contained in reservoir 40. In at least one embodiment, the reservoir 40 may be a catheter bag having a capacity of about 2,000 milliliters (ml). A reservoir 40 of this size may receive about six urinations, assuming an average urination is between about 300 ml and about 400 ml before reaching full capacity. In other embodiments, reservoir 40 may be a tank, a laboratory container, or other such device. Reservoir 40 may also include an exhaust valve 41 for releasing gases from reservoir 40. Reservoir 40 may be releasably coupled to conduit 36 using, for instance, quick connect fitting 38. By releasably coupling reservoir 40 to conduit 36, reservoir 40 may be easily removed and replaced. In other embodiments, reservoir 40 may be permanently attached to conduit 36 using one or more adhesives, mechanical connectors, and other coupling devices.

Urine collection device 10 may include one or more check valves 43 for preventing urine from flowing out of conduit 36 and into urine collection receptacle 12. In at least one embodiment, check valve 43 may be positioned in conduit 36 adjacent to urine collection receptacle 21, as shown in FIG. 1. Alternatively, check valve 43 may be coupled directly to urine collection receptacle 12 or positioned at other locations along conduit 36. Check valve 43 may prevent urine from flowing backwards through conduit 36 and into the urine collection receptacle 12 after the human has finished using urine collection device 10.

In at least one embodiment, the check valve 43 may be attached directly to the urine collection receptacle 12. In this position, the check valve 43 may prevent urine that has passed through the urine collection receptacle 12 and into the conduit 36 from backflowing into the urine collection receptacle 12 in the event the urine collection receptacle is moved lower in elevation than the reservoir 40.

Urine collection device 10 may also include a pump 42 for moving urine from the urine collection filter 12 to reservoir 40. Pump 42 preferably transports urine from the urine collection filter 12 to reservoir 40 through conduit 36 without components of the pump contacting the urine. In one embodiment, pump 42 is a peristaltic pump that allows conduit 36 to be placed in contact with pump 42 without urine contacting components of pump 42. More specifically, conduit 36 is placed in pump 42 by moving a lever 44, which in turn opens a cavity 46 for receiving conduit 36. Conduit 36 is placed in cavity 46 and lever 44 is rotated to secure conduit 36 in pump 42. During operation, rollers (not shown) compress the conduit 36 is rapid succession and create a vacuum in the conduit 36.

Use of the peristaltic pump 42 prevents contamination of the pump 42 with urine. In addition, the configuration of the urine collection device 10 prevents the contamination of components other than the conduit 36, the check valve 43, the reservoir 40, and the urine collection receptacle 12. These components that are in contact with urine during use of the urine collection device 10 may be cleaned with disinfectants. In addition, the components may be replaced quickly and easily. Thus, setup time between usage by different humans is minimal.

Pump 42 draws urine from urine collection receptacle 12 and deposits the urine in reservoir 40. Pump 42 may be operated at varying speeds and may be controlled using a dial 48 or other device. In at least one embodiment, the pump 42 may operate between about 200 revolutions per minute (rpm) and about 300 rpm. Pump 42 may be powered by batteries, which may or may not be rechargeable, or with an alternating current (AC) power source such as power that is typically available from a public utility and supplied through a wall outlet. The pump 42 may include a safety switch 45 for preventing the pump 42 from running while the pump 42 is open and thereby exposing the cavity 46.

Urine collection device 10 may include a stand 50 for supporting pump 42, reservoir 40, and urine collection receptacle 12. Stand 50 may include a center support shaft 52 coupled to a plurality of wheels 54. Wheels 54 may include, but are not limited to, caster wheels. Wheels 54 enable the urine collection device 10 to be portable. Pump 42 may be releasably coupled to shaft 52 so that the height of pump 42 and reservoir 40 can be adjusted. Stand 50 may also include a container 56 coupled to stand 50 for supporting reservoir 40. Stand 50 may have a bottom and may or may not have side walls. Stand 50 preferably is light weight and easily transportable. Stand 50 may also include a towelette dispenser 58. Towelette dispenser 58 may be releasably attached to stand 50 and may be configured to receive a conventional tissue box.

In an alternative embodiment, the urine collection device 10 may not include the stand 50. Rather, the urine collection device 10 may be mounted to a wall or other structure. For instance, the urine collection device 10 may be mounted to a wall in a hospital room or other medical facility or to a wall in a home.

Urine collection device 10 may also include a support device 60 that is configured to support urine collection receptacle 12 when urine collection receptacle is not in use. In one embodiment, support device 60 includes two or more prongs capable of receiving urine collection receptacle 12.

In another embodiment, support device 60 may include a plate having a hole capable of receiving the urine collection receptacle 12. The hole is sized to receive the urine collection receptacle 12 but is not larger than the width of the urine collection receptacle 12.

Urine collection device 10 may include an on/off switch 62 for actuating pump 42. In one embodiment, on/off switch 62 is actuated by moving support device 60. Support device 60 may be configured so that on/off switch 62 is closed when urine collection receptacle 12 is removed from support device 60. Closing on/off switch 62 activates pump 42. Conversely, on/off switch 62 is opened and pump 42 is shut off when urine collection receptacle 12 is placed back on support device 60.

Configuring the on/off switch 62 in this manner enables the urine collection device 12 to be operated automatically. In other words, a human need only remove the urine collection receptacle from the support device 60 and into position between the human's legs. Once in position, the human need only urinate and replace the receptacle on the support device 60. The pump is activated with the receptacle 12 is removed from the support device 60 and deactivated when placed back on the support device 60. In at least one embodiment, a delay relay may be used so that the pump 42 may continue to run for a period, such as, about 10 seconds, after the receptacle 12 has been hung on the support device 60 to pump any remaining urine in the receptacle 12 to the reservoir 40.

Urine collection device 10 is configured to be operated by a human but may also be operated by an assistant, such as a nurse, to remove urine from a human. Urine collection device 10 should be checked before use to ensure that a proper urine collection receptacle 12, either male version 14, a female version, or unisex version 24, is attached. If urine collection receptacle 12 needs to be changed, urine collection receptacle 12 may be changed by disconnecting quick connect fitting 38 and connecting the appropriate urine collection receptacle 12.

A human may activate urine collection device 10 by removing urine collection receptacle 12 from support device 60. Urine collection receptacle 12 should be placed proximate to the human's urethra to capture urine as the urine is expelled from the urethra. Once the human begins to urinate, urine is collected in urine collection receptacle 12. Pump 42 draws urine from urine collection receptacle 12 and pumps the urine into reservoir 40. Prostrate humans may place the urine collection receptacle 12 between the human's legs. The receptacle 12 may be configured such that the urine collects in the collection neck 110 and drains through the check valve 43 into the conduit 36. After the human has finished urinating, urine collection receptacle 12 is placed on support device 60, which turns pump 42 off. The urine collected in reservoir 40 may be emptied from reservoir 40 or reservoir 40 may be disconnected from conduit 36 at quick connect fitting 38 and disposed. A replacement reservoir 40 may be coupled to quick disconnect fitting 38.

The foregoing is provided for purposes of illustrating, explaining, and describing embodiments of this invention. Modifications and adaptations to these embodiments will be apparent to those skilled in the art and may be made without departing from the scope or spirit of this invention.

We claim:

1. A urine collection device,
    a urine collection receptacle configured to receive urine from a human and having an inlet formed from an upper surface and a lower surface, wherein the upper surface is positioned at an angle between about five degrees and about 35 degrees relative to the lower surface;
    a reservoir for collecting the urine received by the urine collection receptacle, wherein the reservoir is portable and is in fluid communication with the urine collection receptacle through a conduit;
    a pump capable of pumping a fluid without contacting the fluid, wherein the pump is in contact with a portion of the conduit between the urine collection receptacle and the reservoir for pumping urine from the urine collection receptacle to the reservoir; and
    an on/off switch coupled to a support device for supporting the urine collection receptacle when the wine collection receptacle is not in use and configured to turn the pump on when the urine collection receptacle is removed from the support device.

2. The urine collection device of claim 1, further comprising a portable frame for supporting the urine collection device.

3. The urine collection device of claim 2, wherein the portable frame further comprises a plurality of wheels coupled to the frame.

4. The urine collection device of claim 2, wherein the portable frame further comprises a container for holding cleaning products.

5. The urine collection device of claim 1, wherein the urine collection receptacle is releasable coupled to the conduit using a quick release fitting.

6. The urine collection device of claim 1, wherein the upper surface is positioned at an angle of about 25 degrees relative to the lower surface.

7. The urine collection device of claim 1, wherein the urine collection receptacle further comprises a neck for collecting urine to be pumped to the reservoir, wherein the neck extends below a lower edge of the inlet.

8. The urine collection device of claim 1, wherein the urine collection receptacle further comprises a seal around a perimeter of an inlet of the urine collection receptacle.

9. The urine collection device of claim 1, wherein the urine collection receptacle further comprises a handle for enabling a user to position the receptacle between the user's legs.

10. The urine collection device of claim 1, wherein the conduit is attached to the urine collection receptacle at a corner of the urine collection receptacle.

11. The urine collection device of claim 1, further comprising a safety switch for preventing the pump from running while the pump is in an open position.

12. The urine collection device of claim 1, wherein the pump is a peristaltic pump.

13. The urine collection device of claim 1, wherein the conduit is a flexible conduit.

14. The urine collection device of claim 13, wherein the conduit is transparent.

15. The urine collection device of claim 1, wherein the reservoir is connected to the conduit with a quick release fitting.

16. The urine collection device of claim 1, wherein the reservoir is transparent and marked to indicate the volume of urine contained in the reservoir.

17. The urine collection device of claim 1, wherein the reservoir includes an exhaust port.

18. The urine collection device of claim 1, wherein the pump is operable at varying speeds.

19. The urine collection device of claim 18, further comprising a check valve coupled to the urine collection receptacle.

20. A urine collection device,
a urine collection receptacle configured to receive urine from a human and having an inlet formed from an upper surface and a lower surface, wherein the upper surface is positioned at an angle between about five degrees and about 35 degrees relative to the lower surface;
a reservoir for collecting the urine received by the urine collection receptacle, wherein the reservoir is portable and is in fluid communication with the urine collection receptacle through a conduit;
a pump capable of pumping a fluid without contacting the fluid, wherein the pump is in contact with a portion of the conduit between the urine collection receptacle and the reservoir for pumping urine from the urine collection receptacle to the reservoir; and
a safety switch for preventing the pump from running while the pump is in an open position.

21. The urine collection device of claim 20, wherein
the pump comprises a peristaltic pump capable of pumping a fluid without contacting the fluid, wherein the peristaltic pump is in contact with a portion of the conduit between the urine collection receptacle and the reservoir for pumping urine from the urine collection receptacle to the reservoir.

22. The urine collection device of claim 21, further comprising a portable frame for supporting the urine collection device.

23. The urine collection device of claim 21, wherein the portable frame further comprises a container for holding cleaning products.

24. The urine collection device of claim 21, wherein the urine collection receptacle is releasable coupled to the conduit using a quick release fitting.

25. The urine collection device of claim 21, wherein the upper surface is positioned at an angle of about 25 degrees relative to the lower surface.

26. The urine collection device of claim 21, wherein the urine collection receptacle further comprises a neck for collecting urine to be pumped to the reservoir, wherein the neck extends below a lower edge of a seal.

27. The urine collection device of claim 21, wherein the urine collection receptacle further comprises a seal around a perimeter of an inlet of the urine collection receptacle.

28. The urine collection device of claim 21, wherein the urine collection receptacle further comprises a handle for enabling user to position the receptacle between the user's legs.

29. The urine collection device of claim 21, wherein the conduit is attached to the urine collection receptacle at a corner of the urine collection receptacle.

30. The urine collection device of claim 21, further comprising an on/off switch coupled to a support device for supporting the urine collection receptacle when the urine collection receptacle is not in use and configured to turn the pump on when the urine collection receptacle is removed from the support device.

31. The urine collection device of claim 21, wherein the reservoir is connected to the conduit with a quick release fitting.

32. The urine collection device of claim 21, wherein the reservoir is transparent and marked to indicate the volume of urine contained in the reservoir.

33. The urine collection device of claim 21, further comprising a check valve coupled to the urine collection receptacle.

* * * * *